US010092268B2

(12) United States Patent
Krimsky et al.

(10) Patent No.: US 10,092,268 B2
(45) Date of Patent: Oct. 9, 2018

(54) METHOD AND APPARATUS TO MONITOR PHYSIOLOGIC AND BIOMETRIC PARAMETERS USING A NON-INVASIVE SET OF TRANSDUCERS

(71) Applicants: William Krimsky, Bel Air, MD (US); Ashish Purekar, Silver Spring, MD (US); Gregory Hiemenz, Silver Spring, MD (US)

(72) Inventors: William Krimsky, Bel Air, MD (US); Ashish Purekar, Silver Spring, MD (US); Gregory Hiemenz, Silver Spring, MD (US)

(73) Assignee: INNOVITAL LLC, Calverton, MD (US)

(*) Notice: Subject to any disclaimer, the term of this patent is extended or adjusted under 35 U.S.C. 154(b) by 452 days.

(21) Appl. No.: 14/309,347

(22) Filed: Jun. 19, 2014

(65) Prior Publication Data

US 2014/0378849 A1     Dec. 25, 2014

Related U.S. Application Data

(60) Provisional application No. 61/836,773, filed on Jun. 19, 2013.

(51) Int. Cl.

| A61B 5/02 | (2006.01) |
|---|---|
| A61B 7/02 | (2006.01) |
| A61B 5/0456 | (2006.01) |
| A61B 5/0205 | (2006.01) |
| A61B 5/08 | (2006.01) |

(Continued)

(52) U.S. Cl.
CPC .............. *A61B 7/026* (2013.01); *A61B 5/01* (2013.01); *A61B 5/0205* (2013.01); *A61B 5/0456* (2013.01); *A61B 5/053* (2013.01); *A61B 5/0809* (2013.01); *A61B 5/14552* (2013.01); *A61B 5/0245* (2013.01); *A61B 5/02055* (2013.01); *A61B 5/14542* (2013.01)

(58) Field of Classification Search
CPC ........................... A61B 5/0205; A61B 5/0402
See application file for complete search history.

(56) References Cited

U.S. PATENT DOCUMENTS

| 6,149,595 | A | * | 11/2000 | Seitz | ....................... | A61B 8/065 |
|---|---|---|---|---|---|---|
| | | | | | | 600/438 |
| 6,368,283 | B1 | * | 4/2002 | Xu | ...................... | A61B 5/0205 |
| | | | | | | 600/485 |
| 2011/0093027 | A1 | * | 4/2011 | Renesto | ............... | A61B 5/0468 |
| | | | | | | 607/9 |

\* cited by examiner

*Primary Examiner* — Michael D Abreu
(74) *Attorney, Agent, or Firm* — Baker Donelson, PC; Royal W. Craig (57) ABSTRACT

Method and apparatus for quantitative and qualitative determination of heart rate, stroke volume, cardiac output, and central fluid volume. Phonocardiography based technique using multiple transducers and multi-sensor processing algorithms provides a non-invasive method of evaluating the output of the heart. This basic system coupled with additional sensor elements provides a wide range of potential capabilities. A system comprising these techniques in a wearable form provides a non-invasive method of determining hydration status and blood volume status. Phonocardiography augmented with multi-sensor signal processing techniques improves signal quality to analyze heart sounds and associated features (e.g. S1 and S2, amongst others). Noise compensation and cancellation techniques for phonocardiography further improve signal to noise ratio to reject external disturbances.

17 Claims, 7 Drawing Sheets

(51) Int. Cl.
  *A61B 5/01* (2006.01)
  *A61B 5/1455* (2006.01)
  *A61B 5/053* (2006.01)
  *A61B 5/0245* (2006.01)
  *A61B 5/145* (2006.01)

| Case | EUH | DEH1 | DEH2 | DEH3 | DEH4 | REC1 | REC2 |
|---|---|---|---|---|---|---|---|
| Weight Loss (%) | 0.0% | -0.3% | -0.8% | -1.3% | -1.7% | -0.4% | -0.4% |
| Heart Rate (bpm) | 64 | 95 | 105 | 97 | 104 | 115 | 102 |
| BP (mmHg) | 112/77 | 104/78 | 114/74 | 115/81 | 119/75 | 107/75 | 114/76 |
| O2 Sat (%) | 97% | 95% | 92% | 95% | 96% | 97% | 96% |

METHOD AND APPARATUS TO MONITOR PHYSIOLOGIC AND BIOMETRIC PARAMETERS USING A NON-INVASIVE SET OF TRANSDUCERS

CROSS-REFERENCE TO RELATED APPLICATION(S)

The present application derives priority from U.S. Provisional Patent Application 61/836,773 filed Jun. 19, 2013.

BACKGROUND OF THE INVENTION

Field of the Invention

The present invention relates to a method and apparatus for monitoring hemodynamics in the human body, and more particularly to a system using non-invasive measurements including phonocardiography to monitor physiological parameters related to hemodynamics.

Description of the Background

Determination of central fluid and blood volume and monitoring of hemodynamics is useful in a wide variety of medical contexts including physical performance monitoring, the assessment, prevention and treatment of dehydration, fatigue alleviation, wound management, fluid resuscitation, detection of cardiac abnormalities, monitoring of cardiac function, as well as in the diagnosis and management of critical illness.

One area of particular interest is the ability to non-invasively detect disorders related to central fluid and central blood volume. Existing techniques for blood volume and stroke volume determination typically provide useful information in tightly controlled environments such as laboratories or medical facilities. However, these techniques often require a degree of 'invasiveness' and suffer when applied outside of a tightly controlled environment. As an example, central venous pressure, long considered to be the gold standard in monitoring central fluid volume and guiding fluid resuscitation, requires a highly invasive central venous catheter and thus is not suitable outside of controlled medical facilities. A non-invasive methodology to robustly and reliably determine blood volume and cardiac output in a variety of settings is needed since existing techniques are not practical.

Additionally, a non-invasive monitoring system that can be embedded in an article of clothing would be highly desirable and useful given the variety of situations where physiologic and biometric monitoring can be employed. The need to integrate a system into a wearable device places restrictions on the size, power, and weight. Again, current technologies for monitoring of hemodynamics non-invasively are not particularly suitable in this regard and typically do not provide accurate results.

Phonocardiography

During the cardiac cycle, blood moves through the different chambers of the heart due to pressure differences between the chambers and accompanying vessels. Valves in the heart prevent the backflow of blood and open and close based on pressure differences. Certain heart sounds occur primarily due to the closure of the heart valves. This snapping action produces sound waves which travel through the blood and thoracic tissue to the surface where auscultation devices are used.

Phonocardiography techniques evaluate and examine the sounds which the heart produces during the course of the cardiac cycle. The phonocardiograph waveform can be determined using transducer(s) attached or mounted on the surface of the body. In healthy subjects the prominent features of the phonocardiogram are the S1 and S2 components ("lub" and "dub", respectively) which mark the beginning and end of the ventricular contraction. The S1 component of the phonocardiogram marks the closure of the mitral and tricuspid valves and the S2 component marks the closure of the aortic and pulmonic valves.

The phonocardiogram wave form may also display additional components (e.g., murmurs, rubs and gallops) besides the S1 and S2 components and their presence may be benign or serve as indicators of abnormalities.

There is a long and robust history of using hearts sounds and phonocardiography to diagnose cardiac aberrancies and specific valvular abnormalities, dating back to the late 1940s. Over the next several decades Phonocardiography evolved to be an effective and widely used technique in clinical practice before the advent of other methods to evaluate the heart and its function such as ultrasound and coronary angiography, but its prevalence has diminished as a consequence of several issues. As noted by Sprague, in "The Clinical Value of Phonocardiography" (1954), the clinical value of phonocardiography suffered from the limitation of then existing analog electronics. Interest was regained in 1990s with the advent more advanced digital signal processing techniques to the analysis of heart sounds. See, Brusco and Nazeran, Development of an Intelligent PDA-based Wearable Digital Phonocardiograph, Engineering in Medicine and Biology 27th Annual Conference (2005). Examples of prior art phonocardiography systems include:

United States Patent Application 20130338724 by Joo et al. published Dec. 19, 2013 shows a pulse detection system that measures two parameters such as phonocardiogram (PCG) signals, electrocardiogram (ECG) signals, patient impedance signals, piezoelectric signals, and accelerometer signals, and analyzes the combined signals for features indicative of the presence of a cardiac pulse. The medical device is wearable (electrodes).

PCT Publication number WO2013184315 filed May 15, 2013 by Bedingham et al. (3M) shows a phonocardiogram adapted to combine an acoustic signal and the electrical signal detected over a plurality of cardiac cycles of the heart.

U.S. Pat. No. 5,012,815 to Bennett, Jr. et al. issued May 7, 1991 shows a dynamic spectral phonocardiograph that summarizes time-dependent changes in the heart sounds based on a Fourier transform of heart sounds as a function of time.

U.S. Pat. No. 5,812,678 to Scalise et al. issued Sep. 22, 1998 shows a noise-canceling phonocardiographic sound monitoring system.

U.S. Pat. No. 5,638,823 to Akay et al. (Rutgers) issued Jun. 17, 1997 shows a system and method for noninvasive detection of coronary artery disease by phonogrammetric analyses.

U.S. Pat. No. 8,478,391 to Scheiner et al. (Cardiac Pacemakers, Inc.) issued Jul. 2, 2013 and related U.S. Pat. No. 8,663,123 issued Mar. 4, 2014 show an apparatus and method for outputting heart sounds using an implantable system that transmits to an external system.

United States Patent Application 20100094152 by Semmlow published Apr. 15, 2010 shows a phonocardiographic system and method for acoustic detection of coronary artery disease.

U.S. Pat. No. 6,149,595 to Seitz et al. issued Nov. 21, 2000 shows a noninvasive apparatus and method for the determination of cardiac valve function.

U.S. Pat. No. 7,666,144 to Cohen et al. (Michigan State University) issued Feb. 23, 2010 shows a method and apparatus for determining proportional cardiac output (CO), absolute left atrial pressure (LAP), and/or other important hemodynamic variables from a contour of an RVP waveform attained by a phonocardiogram.

U.S. Pat. No. 8,290,577 to Brooks et al. issued Oct. 16, 2012 shows a method and apparatus for enhanced fiducial point determination and non-invasive hemodynamic parameter determination from phonocardiography.

United States Patent Application 20050222515 Polyshchuk et al. (Biosignetics Corporation) published Oct. 6, 2005 shows techniques of interpreting cardiovascular sounds with a self-referencing feature based on stored phonocardiograms.

U.S. Pat. No. 8,348,852 to Bauer et al. (Inovise Medical, Inc.) issued Jan. 8, 2013 shows heart-activity sound monitoring using an acoustic sensor resonant at S1, S2, S3, S4 heart-sound frequencies, using a wave generator to stimulate it, and observing over time any time-based differences which exist between the two as being representations of the subject's S1, S2, S3, S4 heart sounds, and from such interpreted differences, producing a utility output associated with the subject.

Studies by NASA in the 1980's included phonocardiography as one method of thoroughly evaluating astronaut health both pre- and post-flight (Bergman, Stuart, Robert Johnson, and G. Wyckliffe Hoffler. "Evaluation of the Electromechanical Properties of the Cardiovascular System After Prolonged Weightlessness." In Biomedical Results from Skylab, 351-365, 1977). Buried within this data a correlation between parameters identified via phonocardiography and volume status can be found. During Lower Body Negative Pressure testing of the astronauts, a significant difference in the ventricular ejection time as indicated by the time between S1 and S2 heart sounds were observed between normal conditions and Lower Body Negative Pressure conditions.

Unfortunately the challenges with phonocardiography based techniques included a need for highly sensitive equipment and a need for exquisitely controlled testing conditions. As a result, phonocardiography has more recently fallen out of clinical practice in favor of these other techniques. It is important to note, however, that these current techniques require bulky, expensive, and high power equipment along with a highly trained user.

Hemodynamics and Blood Volume Status

Ventricular contraction in the cardiac cycle results in the movement of blood from the heart into the circulatory system. The QRS complex is a known feature of the electrocardiogram and can be used as a reference for the cardiac cycle. Most notably, the R wave is a prominent upward deflection in the signal. The start and end of ventricular contraction is closely and physically linked with the S1 and S2 heart sounds. Assessment of blood volume and cardiac output may be performed using heart sounds.

Figure 7:
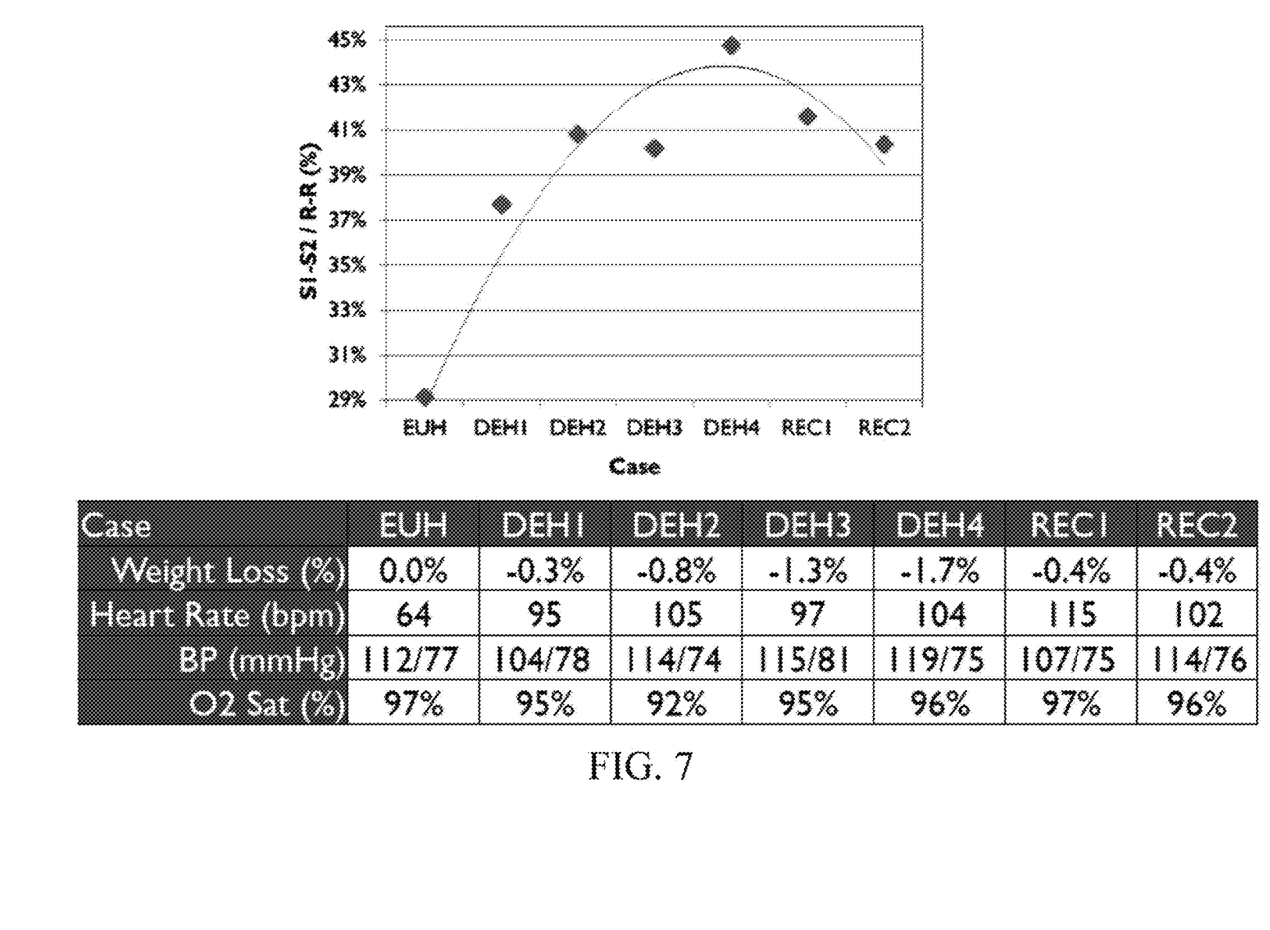
FIG. 7 correlates the PSTI results to seven physical states of a test patient subjected to exercise to induce dehydration.

In order to validate that events within a cardiac cycle are affected by dehydration, the inventors herein first conducted proof-of-principle testing to evaluate the effect that dehydration would have on Phonocardiographic Systolic Time Intervals (PSTI; i.e. S1-S2 time divided by heart beat period). Body weight and PCG waveforms (applying an off the shelf microphone) were collected on a human test subject before and during an intensive workout routine. Gross physiological parameters from the test including weight loss, hear rate, blood pressure, and blood oxygenation for euvolemic and dehydrated states are shown in FIG. 7. Data reduction from phonocardiography readings was used to determine the PSTI for each state over a 1 minute period. The PSTI for a normally euhydrated state, dehydrated state at up to 1.7% loss in body mass, and recovered state is shown in FIG. 7. The change in S1-S2 time, normalized for heart rate, is significantly higher in the dehydrated state, indicating a change in the hemodynamics associated with dehydration. This initial testing demonstrated high sensitivity to even mild dehydration—over five times more sensitive than standard clinical assessment. In the testing data, the PSTI is determined using time based features corresponding to the S1 and S2 from the phonocardiography transducer normalized by the time between the R wave and subsequent R wave in the electrocardiogram. Similar information may be determined using the S1 and subsequent S1 in the phonocardiogram for normalization.

SUMMARY OF THE INVENTION

The present invention includes a method and apparatus for the detection of a variety of conditions symptomatic of central fluid and blood volume, such as dehydration, hypovolemia or hypervolemia, detection of cardiac abnormalities, wound management, and/or guidance of fluid resuscitation.

It is another object to detect these conditions by monitoring and assessment of central fluid and blood volume, cardiac output, and stroke volume over time by referencing time based features from phonocardiographic signals to cardiac electrical output using a combination of sensors with a robust and reliable methodology in a wearable device.

It is another object to detect the foregoing conditions by referencing intracycle timing features from phonocardiographic signals to intercycle timing.

The first aspect of the invention is a method to monitor and assess central fluid and blood volume and/or cardiac stroke volume by obtaining phonocardiography information using a plurality of sensors and signal processing algorithms.

The second aspect of the invention is a robust methodology to monitor central fluid and blood volume, stroke volume, and/or cardiac output using a combination of a mathematical model and features from the phonocardiography waveform including, but not limited to, ventricular ejection time, amplitude of the S1 heart sound, and the heart rate.

The third aspect of the invention is the use of multi-sensor processing techniques on multiple phonocardiography transducers to improve signal clarity to allow for accurate determination and extraction of all heart sound features.

The fourth aspect of the invention is the implementation of active or passive noise cancellation technologies to further improve signal to noise on the phonocardiography transducers.

The fifth aspect of the invention is the use of sensor fusion techniques which use sensors of different types to provide a robust evaluation of cardiac function including, but not limited to, stroke volume, cardiac output, and central fluid and blood volume. Such additional sensors may include, but not limited to, electrical activity, electrodes for impedance cardiography and measuring changes in thoracic impedance, blood pressure, respiration sensors, blood oximetry sensors, inertial measurement, internal and surface temperature, etc.

The sixth aspect of the invention is the implementation of the method as part of a system including electronics for signal conditioning, data acquisition, processing, display, and communication, and power components.

The seventh aspect of the invention is the integration of the system into a form factor such as an article or clothing or cuff worn on the body.

The eight aspect of the invention is the implementation of algorithms to provide feedback in the form of an alarm or alert to warn of changes in hydration status or blood volume status (hypovolemia or hypervolemia) and guide fluid resuscitation as well as for the assessment and management of other cardiac abnormalities.

The ninth aspect of the invention is the method and apparatus for measuring, storing, and using known baseline physiological data of the wearer of the system for tracking deviations from said baseline.

The tenth aspect of the invention is to utilize machine learning algorithms to assist in determining said baseline and said deviations.

BRIEF DESCRIPTION OF THE DRAWINGS

Other objects, features, and advantages of the present invention become more apparent from the following detailed description of the preferred embodiments and certain modifications thereof when taken together with the accompanying drawings in which.

DETAILED DESCRIPTION OF THE INVENTION

The present invention is a robust, reliable, sensitive, and non-invasive method and system for the detection of conditions symptomatic of central fluid and blood volume, including dehydration, hypovolemia or hypervolemia, cardiac abnormalities, wound management, and/or guidance of fluid resuscitation. The method and system achieves this by referencing time based features from phonocardiographic signals using an improved signal processing algorithm. Such a system can be utilized for monitoring hydration status (e.g., dehydration, electrolyte imbalance), circulating blood volume (e.g. hypervolemia, hypovolemia), and/or guiding fluid resuscitation.

As used herein, "stroke volume" is the volume of blood pumped from the ventricle of the heart into the circulatory system of the body. The stroke volume is the difference between the End Diastolic Volume of the ventricle and the End Systolic Volume of the ventricle.

As used herein, "cardiac output" refers to the volume of blood pumped by the heart and can be determined by the relationship in Equation (1) where CO is the Cardiac Output, SV is the Stroke Volume, and HR is the heart rate.

$$CO = SV \times HR \qquad (1)$$

Overview

Figure 1:
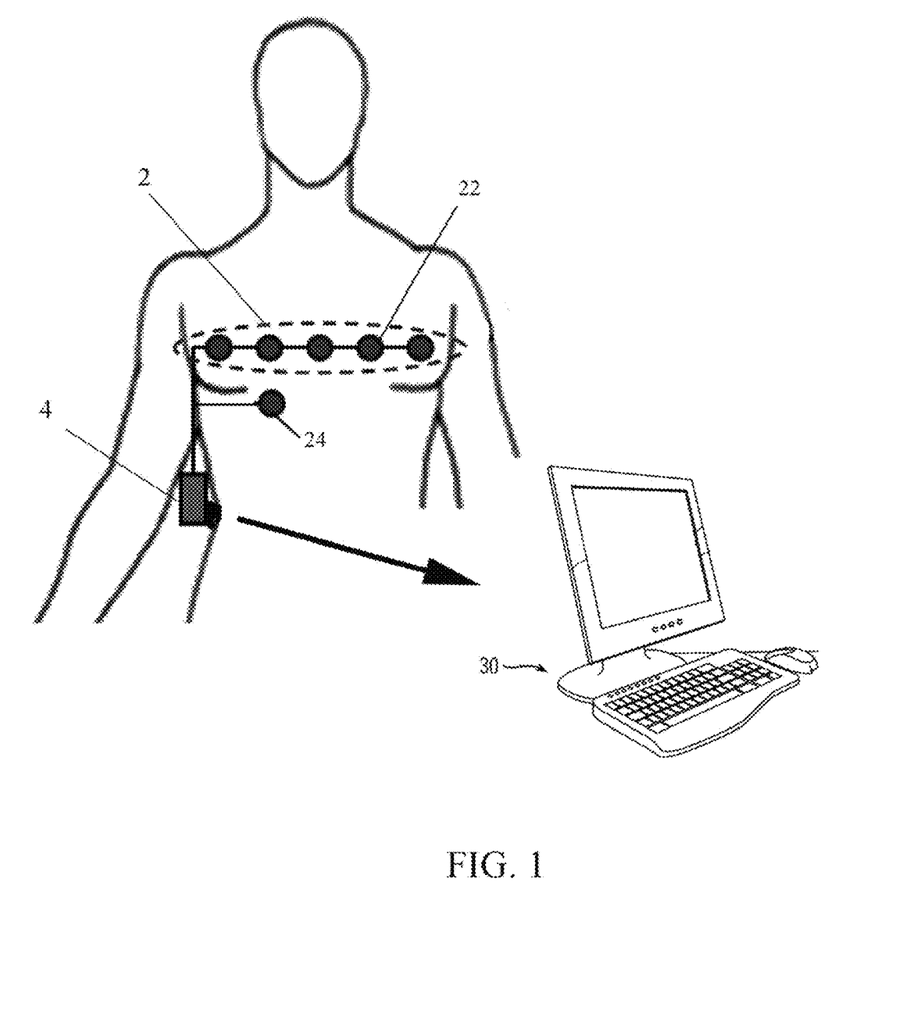
FIG. 1 is a perspective view of an exemplary embodiment of the phonocardiographic system according to the invention.

FIG. 1 is a perspective view of an exemplary embodiment of the phonocardiographic system of the invention, which generally employs a wearable transducer array 2 containing at least one acoustic transducer 22 for generating audio phonocardiographic data that can be read into a computer. The transducer array 2 is preferably integrated into a wearable device such as strap to which wraps around the torso for a wearable and self-contained system. In an embodiment, transducer array 2 may also be equipped with supplemental sensors for providing various other types of feedback, for example an electrical (EKG) transducer 24, and/or an accelerometer such as a MEMS 3-axis motion sensor for monitoring orientation, angular, and linear movement.

The combined signals from transducer array 2 are fed to a data acquisition unit 4 and are stored, and can be transferred in real-time or later to a Host PC 30. Data acquisition unit 4 serves two primary functions: 1) data recording; plus 2) the ability to multiplex the various sensor signals together for recording. The data acquisition unit 4 may be connected to host PC 30 via a cable, or wirelessly, for importing data into the software of the present invention. Alternatively, the data acquisition unit 4 may be combined with a host PC 30 in the form of a smartphone or tablet computer. Thus, host PC 30 may be any suitable laptop or desktop computer, tablet or smartphone, or other processing device running software for implementing the method of the present invention. The Host PC 30 runs software for analyzing the time based features from phonocardiographic signals using an improved signal processing algorithm. In one embodiment, the analytical software references intra-cyclic time-based features from the phonocardiographic signals to inter-cyclic features in order to detect the patient's conditions. In another embodiment, the analytical software references intra-cyclic time-based features from the phonocardiographic signals to inter-cyclic features from any of the other transducer types such as, for example, the an electrical (EKG) transducer 24.

Figure 2:
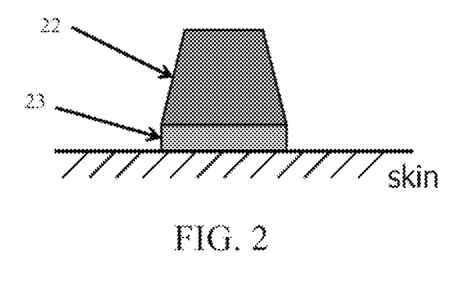
FIG. 2 is a diagram of an exemplary skin-contact transducer.

Phonocardiography transducers 22 convert pressure waves into electrical signals through contact with the skin using a couplant 23 such as air, gel, or water. A diagram of skin-contact transducers is shown in FIG. 2. Candidate transducers include, but are not limited to, microphones or accelerometers. Mechanisms to amplify the pressure waves include bell or diaphragm auscultation devices coupled with the microphones or accelerometers.

Figure 3:
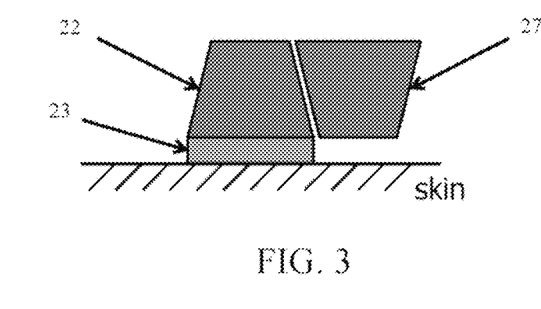
FIG. 3 shows an alternative phonocardiographic transducer configuration that includes a supplemental noise-compensation transducer.

FIG. 3 shows an alternative phonocardiographic transducer configuration that includes a supplemental noise-compensation transducer 27 adjacent to the phonocardiography transducer 22 but not in ski-contact. The signal from the compensation transducer 27 is combined with the phonocardiography transducer 22 through signal processing to remove noise from the environment. In this case, two signals are needed, the phonocardiography transducer 22 and the compensation transducer 27 and noise cancellation is done in real-time though either analog methods or on a processor.

Electrical transducer 24 may be a conventional electrocardiogram (EKG or ECG) transducer. In accordance with the invention the Host PC 30 runs software for analyzing the combined signals by referencing time based features from phonocardiographic signals to cardiac electrical output using an improved signal processing algorithm. One benefit of using a purely phonocardiagraphy-based approach is the ability to quantify heart rate, stroke volume, and cardiac output using a singular technique. However, in this instance a calibration step would need to be conducted in order to identify the stroke volume based on parameters determined from phonocardiography readings. Calibration is optional when referencing time-based features from the phonocardiographic signals to an electrical (EKG) transducer 24 or other transducer. The software method determines central fluid and blood volume, cardiac output, and/or stroke volume based on the foregoing measurements.

Figure 4:
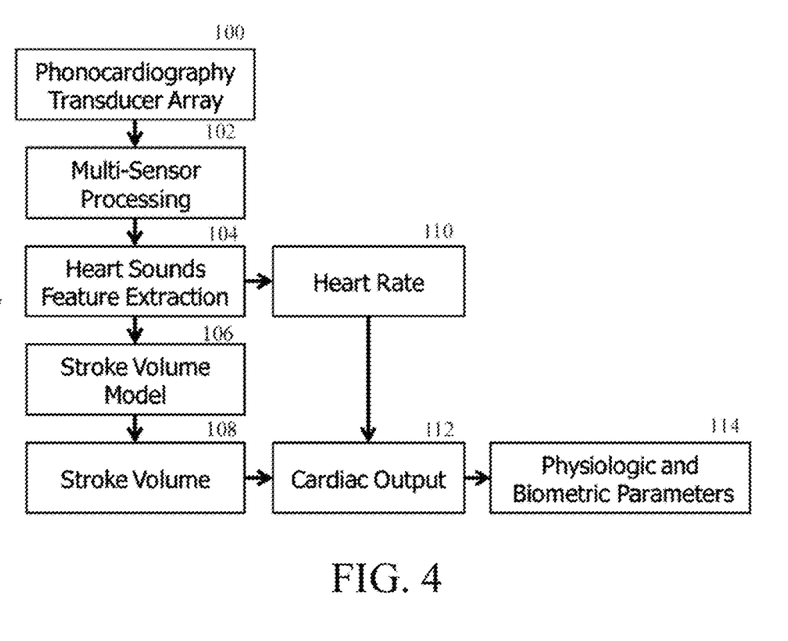
FIG. 4 is a flow diagram of the general software method.

A flow diagram of the general software method configured for determining stroke volume is shown in FIG. 4. At step 100 phonocardiagraphy transducer array 2 converts pressure waves into electrical signals through contact with the skin using a couplant 23. The analog signals are digitized and analyzed by a multi-sensor processor at step 102 and heart sound features (e.g., S1 and S2) are extracted at step 104. Heart rate is derived from the phonocardiography transducer 22 or electrical activity from transducer 24 at step 110. The sound profile is subjected to a stroke volume model at step 106. The model is a mathematical construct to determine an indication of a cardiac stroke volume at step 108, as a function of any one or more parameters including heart rate, systolic time intervals, properties of the S1 heart sound, etc. Both outputs from steps 108, 110 are used to compute cardiac output at step 112. Cardiac output is compared to normal baseline parameters of the individual at step 114, and the result may be used to provide an alert to an external device.

As an alternative to cardiac stroke volume at step 108, the present system can be configured for monitoring hydration status (e.g., dehydration, electrolyte imbalance), circulating blood volume (e.g. hypervolemia, hypovolemia), and/or guiding fluid resuscitation.

Figure 5:
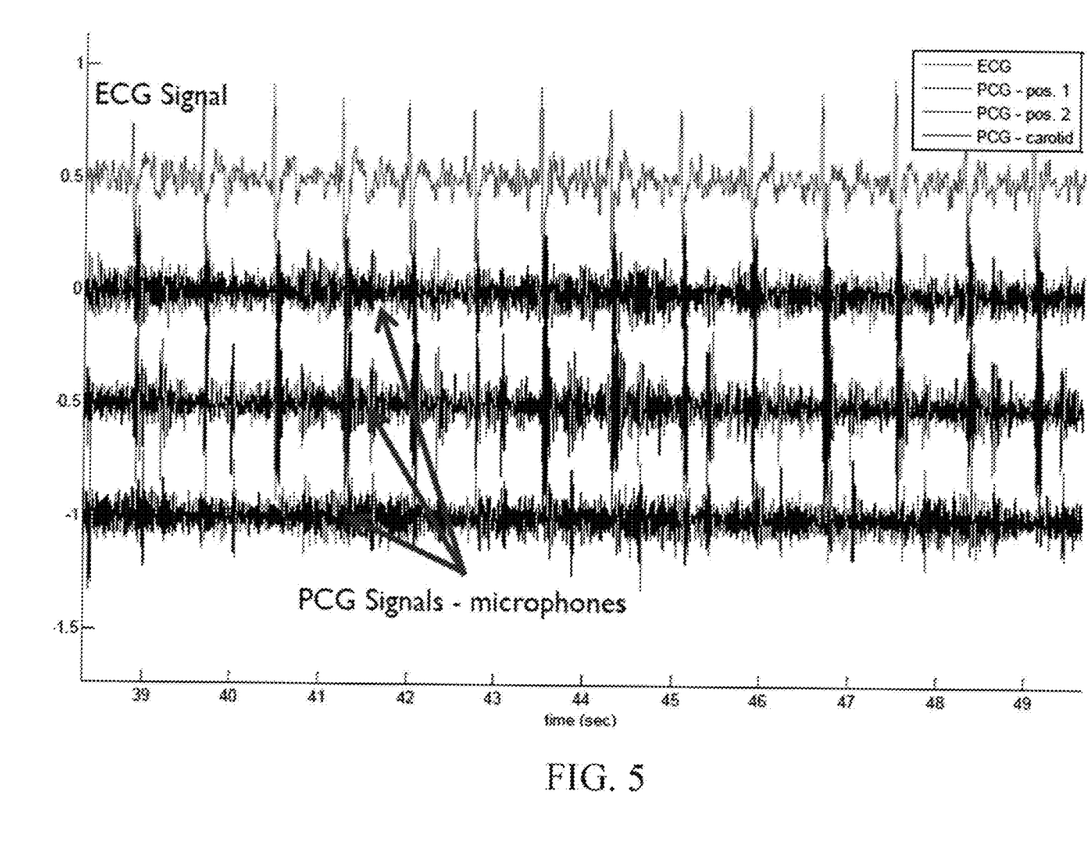
FIG. 5 is a graph of the raw output from a transducer array 2 of three phonocardiography transducers.

FIG. 5 is a graph of the raw output from a transducer array 2 of three phonocardiography transducers 22-1, 2 and 3 and the EKG signal from electrical transducer 24 for comparative purposes, as a function of amplitude over time. Both types of signal are systematic and substantially synchronized.

Figure 6:
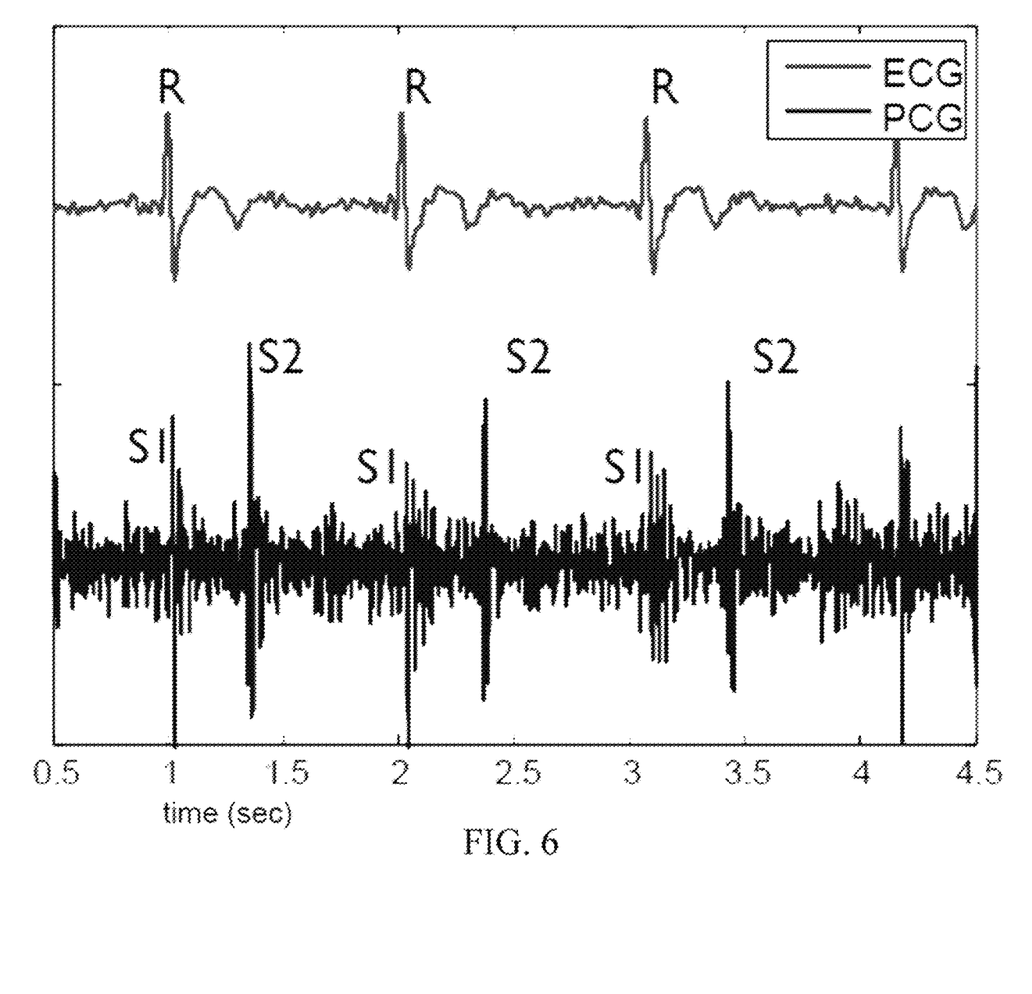
FIG. 6 is a graph of the filtered output from an element in transducer array 2 in reference to the electrical activity where specific features from the waveforms are identified.

FIG. 6 is a graph of the filtered output from a phonocardiography transducer 22-1 from the transducer array 2, as with the EKG signal from electrical transducer 24. Phonocardiography techniques provide a direct indication and measurement of closing of heart valves. A common representation of phonocardiography is the identification of the S1 and S2 heart sounds which represents one heartbeat. The number of beats occurring over a time interval indicates heart rate. Stroke volume from phonocardiography is determined from a combination of different effects. Systolic Time Intervals, the time between S1 and S2 hearts sounds, has shown a correlation with cardiac output. Properties of the S1 heart sound corresponding to closure of the mitral and tricuspid valves have also shown a correlation with cardiac output.

According to one embodiment, the analytical software references intra-cyclic time-based features from the phonocardiographic signals to inter-cyclic features from EKG transducer 24. With reference to FIG. 6, recurring heart sound features S1 and S2 are identified (as per step 104).

Heart rate R is derived from step 110. The software method references time based features from the phonocardiographic signal to cardiac electrical output by calculation of a PSTI statistic as shown below:

$$PSTI = S1 - S2/R - R = Time_{S1-S2}/Time_{R-next\ R}$$

Figure 8:
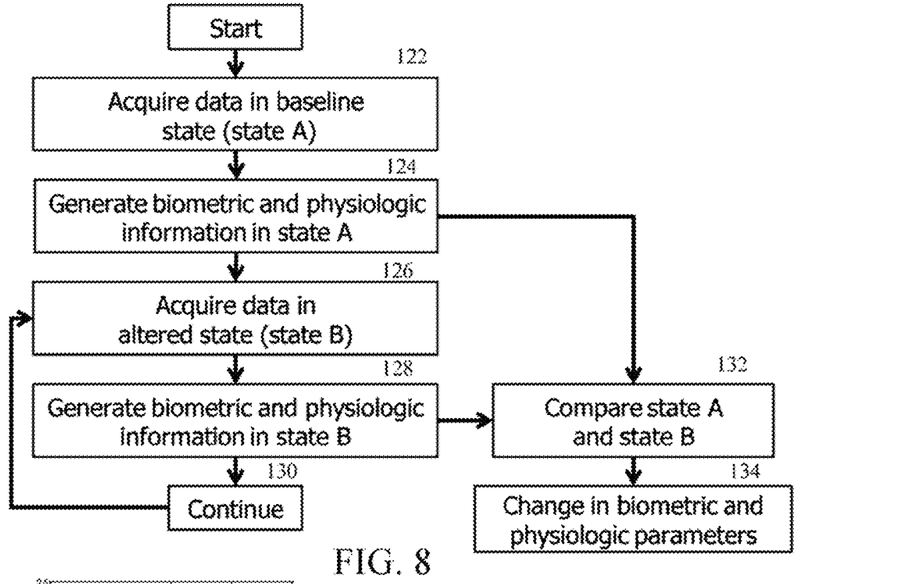
FIG. 8 is a diagram tracking the change in the cardiac output and stroke volume of the heart over time.

FIG. 7 correlates the PSTI results to seven physical states of a test patient subjected to exercise to induce dehydration. The test subject was not given external fluids, yet produced sweat. All data was taken at regular intervals beginning at a normal euvolemic state (EUH), with normal hydration progressing to gradually increasing dehydration from DEH1 to DEH4, followed by rest and fluid intake at REC1 and REC2. At state EUH where weight is normal, heart rate is normal, blood pressure is normal and blood is fully oxygenated, the PSTI statistic is at its lowest 29%. However, as weight decreases below normal, heart rate increases, blood pressure increases, and/or blood oxygen saturation decreases, the PSTI statistic rises, and attains its highest value (96%) at DEH4, correlating most strongly to weight loss. Thus, increasing weight loss is related to loss of fluids and dehydration, and the PSTI statistic serves as a predictor. Another aspect of the invention is the ability to track the change in the cardiac output and stroke volume of the heart over time. A diagram of this process method is shown in FIG. 8. At step 122 data is acquired in a baseline state (state A). At step 124 biometric and physiologic information is generated in state A. At step 126 data is acquired in an altered state (state B). At step 128 biometric and physiologic information is generated in state B. At statistical analysis step 130 the information from the two states is compared, and at step 134 any change in biometric and physiologic parameters is determined. For example, data gathered at either a normal (euvolemic) state a baseline state can form a standard set of data for cardiac output and stroke volume determination at step 124. With continued use and the change of state from the initial condition, a qualitative comparison can be performed with the baseline state at step 134. This method of qualitative comparison provides trending method which can be saved and processed at a later data for quantitative assessment.

In another embodiment, the analytical software references intra-cyclic time-based features from the phonocardiographic signals to inter-cyclic features of the phonocardiographic signals in order to detect the patient's conditions. Recurring heart sound features S1 and S2 are identified (as above per step 104). In this case heart rate R is derived from step 110 from inter-cyclic S1 to S1 features from the phonocardiographic signal for calculation of the same PSTI statistic as shown above.

In addition to referencing the presence of recurring heart sound features S1 and S2 (as above per step 104), the analytical software references may reference the third or fourth heart sound(s) for diagnosis and, more particularly, either the presence and/or absence of third or fourth heart sound features S3 and/or S4 in order to detect the patient's conditions (as above per step 104).

The statistical analysis step 130 may be more comprehensive in order to more accurately detect statistical changes in biometric and physical parameters. In one embodiment, the statistical analysis step employs a data binning process. Data binning helps to reduce the effects of minor observation errors. Generally, original data values which fall in a given small interval, a bin, are replaced by a value representative of that interval, often the central value. It is a form of data aggregation. This aggregation reduces the number of data points (with a loss of information) but also reduces the impact of noise.

Figure 9:
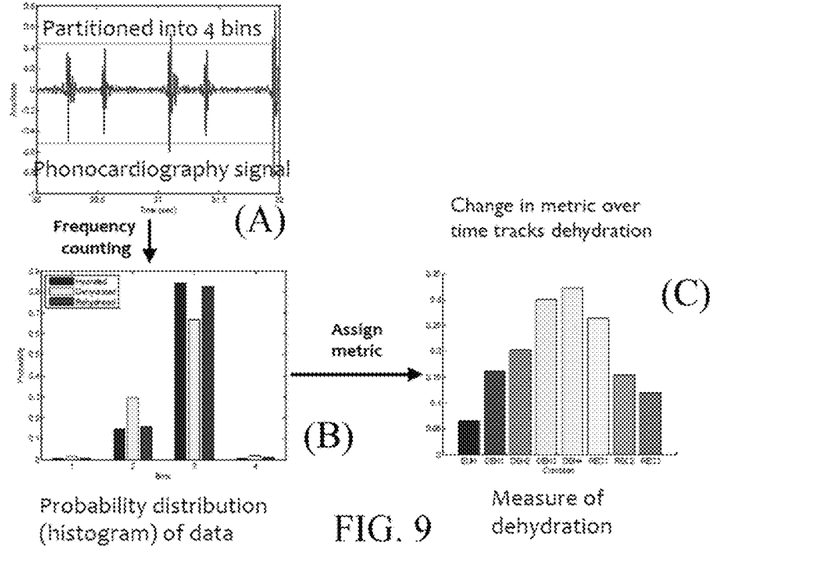
FIG. 9 is a stepwise example of the software data binning process.

FIG. 9 is a stepwise example of the software data binning process of step 130. At (A), the PSTI statistic calculated above is mapped into one of a plurality of bins (here four). At (B), a histogram of the four data bins is compiled which shows the probability distribution of the PSTI statistic falling within one of the four bins. AT (C), the data from (B) is tracked over time, the change in the metric over time is reflective of the physical condition of the patient.

In another embodiment, the statistical analysis step 130 may employ a Fourier analysis, and in another, a least-squares curve-fitting function.

One skilled in the art should understand that any suitable data quantization technique may be used for statistical analysis step 130.

Figure 10:
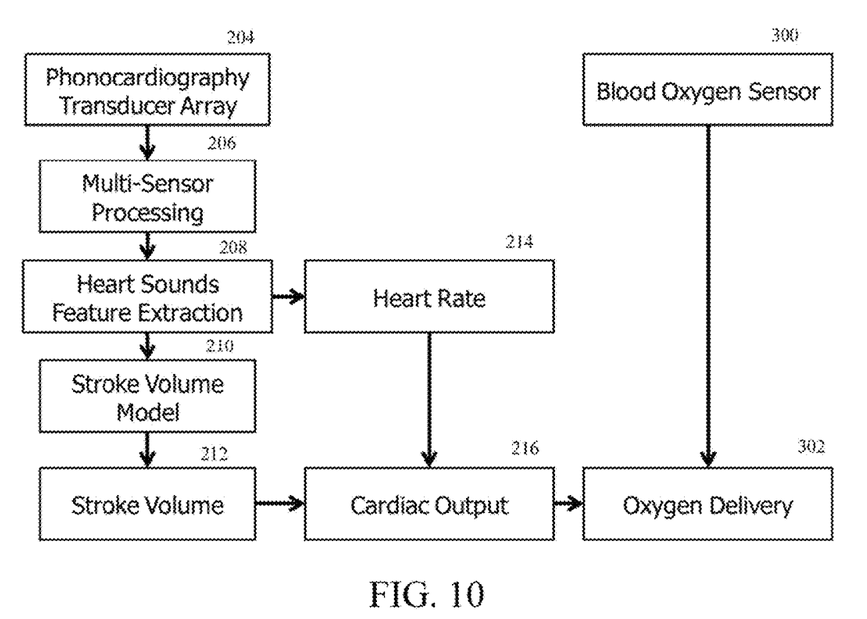
FIG. 10 is a flow diagram describing the process coupled with a blood oxygen sensing unit to determine oxygen delivery to the body.
Figure 11:
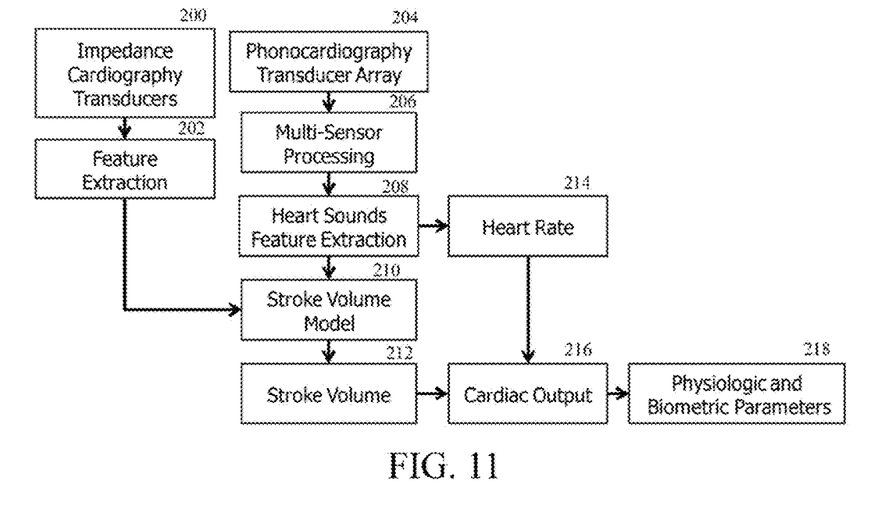
FIG. 11 is a flow diagram describing the process coupled with impedance cardiography sensing unit to determine cardiac output to the body.

Another aspect of the invention is the ability to determine cardiac output and stroke volume using a combination of phonocardiography and impedance cardiography technique (ICG), the ICG sensors being impedance sensors that detect the properties of the blood flow in the thorax. Stroke volume is found using the expression in Equation (2) using a constant, C, the maximum change in the derivative of the impedance cardiogram, and the Ventricular Ejection Time, VET. VET can be determined from heart sounds and is closely related to the difference in time between the S1 and S2 heart sounds. The constant, C, is found from a combination of parameters including the weight of the individual, a baseline impedance, and a representative volume of tissue participating in the impedance cardiogram. Cardiac output is then found using the heart rate and stroke volume as in Equation (1). A diagram of this method is shown in FIG. 10. At step 200 impedance cardiography transducers are employed to take non-invasive hemodynamic measurements. At step 204 a phonocardiography transducer array (array of vibration sensors) is placed noninvasively on the external chest wall. At step 202 features are extracted from the impedance cardiography measurements. At step 206 the phonocardiography measurements are input to a multi-sensor processor and at step 208 features are extracted from the heart sounds. The sound profile is subjected to a stroke volume model at step 210 as described above. Both outputs from steps 202, 208 are used to compute cardiac output at step 216. Cardiac output is compared to normal baseline parameters of the individual at step 218, and the result may be used to provide an alert to an external device.

Further, changes in thoracic impedance as compared to a set of initial conditions including that of a euvolemic baseline can be used to directly track changes in central fluid volume, changes in tissue volume, changes in blood volume, etc.

$$SV = C \times (\partial Z / \partial t)\_max \times VET \qquad (2)$$

Phonocardiography techniques are difficult to implement environments outside of a laboratory or clinical setting due to presence of external noise. Existing methods rely on a singular auscultation device to generate the phonocardiogram waveform. Phased array signal processing techniques are used in antenna and acoustic design to extract salient features from waveforms by combining multiple signals, $v_i(t)$, into a consolidated signal, v(t). A simple method is shown in Equation (3) where the average of the signals is determined. If noise in the signal has a distribution with zero mean, then the simple method of adding multiple signals provides an improvement.

$$v(t) = \frac{1}{N} \sum_1^N v_i(t) \qquad (3)$$

In phased array analysis, the sensor signals are combined into a single signal by introducing constants and time shifts as shown in Equation (4) where $a_i$ and $\Delta t_i$ need to be determined and applied. This signal processing technique allows multiple sensor signals to be combined into a multitude of output signals based on given sets of constants and time shifts.

$$v(t) = \frac{1}{N} \sum_1^N a_i v_i(t + \Delta t_i) \qquad (4)$$

For an array of sensors, the constants, $a_i$, and time shifts, $\Delta t_i$, are determined based on the distribution and orientation of the sensors, the wave propagation properties in the medium, and the position of the source of the sound. For phased array phonocardiography, the equivalent parameters are the distribution of devices on the torso, the acoustic wave propagation properties in the torso, and the position of the heart in the torso. The formulation in Equation (4) is commonly done in a post-processing step after all sensor readings have been gathered and cannot be implemented in a real-time manner.

$$v(t) = \frac{1}{N} \sum_1^N a_i v_i(t) + b_i \int v_i(t) dt \qquad (5)$$

The formulation in Equation (5) has an additional component in the summation including the constant, $b_i$, and the integral of the sensor signals. This formulation effectively adds a phase shift component similar to that accomplished by the time shift in Equation (4). One benefit of this approach is the ability of real-time implementation. Another method of introducing a pure phase shift is the through the use of the Hilbert Transform, H, as shown in Equation (6).

$$v(t) = \frac{1}{N} \sum_1^N a_i v_i(t) + b_i H(v_i(t)) \qquad (6)$$

One of the major benefits of this approach is the ability to adjust the time, or phase shifts, in the sensor signals such that a source can be more heard more cleanly than with a singular measurement device for phonocardiography. Additional signal processing techniques may be implemented with the objective of extracting the true phonocardiography signal from multiple sensors readings. The term multi-sensor signal processing is used to describe the above techniques of combining multiple signals of the same type into a consolidated signal.

Another benefit of the approach is to selectively listen to specific areas within the region of interest by adjusting the constants and time shifts. For phonocardiography, such an approach allows the system to selectively listen to the valves within the heart, the mitral and tricuspid valves and the aortic and pulmonary valves.

Another aspect of the invention is the ability to couple the phonocardiography based method for cardiac output determination with other methods for a variety of different purposes. For example, the invention may be coupled with a blood oxygen sensing unit to determine oxygen delivery to the body. A diagram describing this process is shown in FIG. 10.

At step 204 a phonocardiography transducer array (array of vibration sensors) is placed noninvasively on the external chest wall. At step 202 features are extracted from the impedance cardiography measurements. At step 206 the phonocardiography measurements are input to a multi-sensor processor and at step 208 features are extracted from the heart sounds. The sound profile is subjected to a stroke volume model at step 210 as described above. Both outputs from steps 202, 208 are used to compute cardiac output at step 216. Cardiac output is compared to normal baseline parameters of the individual at step 218. At step 300 a blood oxygen sensor detects blood oxygen level, e.g., concentration of oxygen in the blood. The combined results of step 300 and 216 may be used to control oxygen delivery at step 302.

Additional components of the system comprise (1) signal conditioning electronics, (2) data acquisition to convert analog signals into digital data, (3) data storage of the digital information, (4) processing unit to execute algorithms, (5) communication system consisting of either wired and/or wireless components, (6) display unit to show relevant information to a user, and (7) power subsystem which provides energy to the transducers and electronics through primary or rechargeable batteries. These system components will be common across all embodiments of the envisioned system.

The primary embodiment of the invention is a wearable system comprising an array of phonocardiography transducers. The system can either be coupled directly to the body or integrated into an article of clothing such as a shirt through which contact is established. The phonocardiography components are integrated system components for a wearable and self contained system.

Another embodiment of the invention is the wearable system comprising an array of phonocardiography transducers in device such as a cuff or sleeve which can be worn on an arm or leg.

Another embodiment of the invention is the wearable system comprising an array of phonocardiography transducers along with impedance cardiography transducers in a device such as strap to which wraps around the torso.

Yet another embodiment of the invention is the wearable system comprising an array of phonocardiography transducers along with impedance cardiography transducers in a device such as a cuff or sleeve which can be worn on an arm or leg

We claim:

1. A system to non-invasively monitor the cardiac cycle of a patient and quantify changes in blood volume of said patient over time therefrom, comprising:
   a phonocardiography transducer configured to measure pressure waves originating from said patient's heart function during said cardiac cycle and generate an analog audio signal waveform corresponding to said cardiac cycle;
   a data acquisition unit configured to condition said analog audio signal waveform, convert said analog audio signal waveform to digital data, store said digital data, and communicate said digital data;
   a processor including a non-transitory computer-readable storage device storing a waveform analysis software module comprising a series of computer-readable instructions for analyzing the signal waveforms by the steps of,
      automatically identifying and extracting time based heart sound features and heartbeat period from said digital data over a time interval,
      computing a phonocardiographic systolic time interval (PSTI) metric comprising a function of said extracted time based heart sound features and heart beat period and storing a log of said computed PSTI metric over said time interval;
      monitoring said log of said computed PSTI metric over said time interval to establish a baseline and detect changes from said baseline; and
      presenting said changes in PSTI as a surrogate for changes in blood volume to guide therapeutic treatment.

2. The system according to claim 1, further comprising a secondary transducer employing a non-audio sensing modality configured for generating a complimentary waveform corresponding to said cardiac cycle.

3. The system according to claim 2, wherein said secondary transducer comprises an electrocardiogram transducer to generate an electrical signal waveform corresponding to said cardiac cycle; and
   said waveform analysis software module comprising a series of computer-readable instructions for analyzing the signal waveforms by the additional steps of,
      extracting one or more time based features from said electrical signal waveform, and
      computing a metric comprising a time-based function of the identified time based features from said electrical waveform.

4. The system according to claim 2, wherein said one or more time based features from said phonocardiographic waveform comprise intra-cyclic features and said one or more time based features from said secondary transducer comprise inter-cyclic features.

5. The system of claim 1 further comprising one or more additional transducers for increasing sensitivity.

6. The system of claim 5 whereas said one or more additional transducers includes any one from among a group consisting of thoracic impedance sensor, inertial measurement sensor, respiration sensor, blood oxygen sensor, internal temperature sensor, and surface temperature sensor.

7. The system according to claim 1, wherein said step of extracting time based heart sound features from said digital data comprises S3 or S4 heart sound features.

8. The system according to claim 1, wherein said time based features comprise both intra-cyclic features and inter-cyclic features.

9. The system according to claim 1, wherein said time based features from said phonocardiographic waveform comprises any three or more from among a group consisting of S1, S2, S3, S4, murmurs, rubs, and gallop.

10. The system according to claim 1, wherein said step of extracting time based heart sound features S and S2 from said digital data comprises data binning.

11. The system according to claim 1, wherein said step of analyzing said computed PSTI metric over time comprises a Fourier analysis.

12. The system according to claim 1, wherein said step of analyzing said computed PSTI metric over time comprises curve fitting.

13. The system of claim 1 wherein said phonocardiography transducer comprises a plurality of phonocardiography transducers arrayed in an integrated wearable form.

14. The system of claim 1, further comprising a step of matching said computed PSTI metric to predetermined statistical patterns.

15. The system according to claim 1, wherein said phonocardiography transducer comprises a dual transducer for eliminating noise.

16. The system according to claim 1, wherein said data acquisition unit and said processor are combined in a portable package.

17. The system according to claim 1, wherein said step of extracting one or more time based features from said digital data further comprises identifying the absence of a heart sound chosen from among a group consisting of S1, S2, S3, S4, gallop, rub, & murmurs.

* * * * *